(12) United States Patent
Cappa et al.

(10) Patent No.: US 10,151,669 B2
(45) Date of Patent: *Dec. 11, 2018

(54) SAMPLER AND SAMPLING METHOD FOR MOLTEN MATERIAL

(71) Applicant: Heraeus Electro-Nite International N.V., Houthalen (BE)

(72) Inventors: Guido Cappa, Houthalen (BE); Gerrit Broekmans, Paal (BE)

(73) Assignee: Heraeus Electro-Nite International N.V., Houthalen (BE)

(*) Notice: Subject to any disclaimer, the term of this patent is extended or adjusted under 35 U.S.C. 154(b) by 199 days.

This patent is subject to a terminal disclaimer.

(21) Appl. No.: 15/258,478

(22) Filed: Sep. 7, 2016

(65) Prior Publication Data

US 2016/0377511 A1    Dec. 29, 2016

Related U.S. Application Data (62) Division of application No. 14/264,658, filed on Apr. 29, 2014, now Pat. No. 9,645,055.

(30) Foreign Application Priority Data

Apr. 30, 2013  (DE) .......... 10 2013 207 959
Nov. 29, 2013  (DE) .......... 10 2013 224 565

(51) Int. Cl.
  *G01N 1/12*  (2006.01)
  *G01N 1/14*  (2006.01)
  (Continued)

(52) U.S. Cl.
  CPC .......... *G01N 1/125* (2013.01); *B01L 3/502* (2013.01); *G01N 1/1409* (2013.01);
  (Continued)

(58) Field of Classification Search
  CPC ............. G01N 2291/0252; B01L 3/502; B01L 2200/0684; B01L 2300/0681; B01L 2300/0832; B01L 2400/0463
  (Continued)

(56) References Cited

U.S. PATENT DOCUMENTS 2,336,075 A    12/1943  Gerhard
2,869,370 A    1/1959   Pagonis
(Continued)

FOREIGN PATENT DOCUMENTS

CN    102788715 A    11/2012
DE    15 40 556 U    4/1976
(Continued)

OTHER PUBLICATIONS

Office Action dated Jul. 30, 2013 in German Appln. Ser. No. 10 2013 207 959.1.
(Continued)

*Primary Examiner* — Daniel S Larkin
*Assistant Examiner* — David L Singer
(74) *Attorney, Agent, or Firm* — Panitch Schwarze Belisario & Nadel LLP (57) ABSTRACT

A sampler has a sample chamber for a sample forming from a molten material, at least one lower cooling body, at least one upper cooling body, at least one inner cooling body, and at least one filling part. The sample chamber is surrounded jointly at least by the lower cooling body and the inner cooling body, such that at least the sample chamber can be cooled by at least the lower and inner cooling bodies. The filling part merges into the sample chamber by a filling opening. Between a region of the outer surface of the inner cooling body and a region of the outer surface of the upper cooling body opposite the outer surface of the inner cooling body, the sampler has at least one gap for conducting at least (Continued)

one gas. The volume of the respective cooling bodies is larger than the volume of the gap.

17 Claims, 5 Drawing Sheets

(51) Int. Cl.
  *G01N 33/20* (2006.01)
  *B01L 3/00* (2006.01)

(52) U.S. Cl.
  CPC .... *G01N 33/206* (2013.01); *B01L 2200/0684* (2013.01); *B01L 2300/0681* (2013.01); *B01L 2300/0832* (2013.01); *B01L 2400/0463* (2013.01); *Y10S 73/09* (2013.01)

(58) Field of Classification Search
  USPC .............................................. 73/377; 75/382
  See application file for complete search history.

(56) References Cited

U.S. PATENT DOCUMENTS

| | | | |
|---|---|---|---|
| 3,315,529 | A | 4/1967 | Feichtinger |
| 3,460,393 | A | 8/1969 | Putnam |
| 3,646,816 | A | 3/1972 | Hance et al. |
| 3,813,944 | A | 6/1974 | Ryntz, Jr. et al. |
| 3,881,355 | A | 5/1975 | Nelson et al. |
| 3,950,992 | A | 4/1976 | Hance |
| 3,974,698 | A | 8/1976 | Scott, Jr. |
| 4,046,016 | A | 9/1977 | Hackett |
| 4,557,152 | A | 12/1985 | Plessers et al. |
| 4,732,477 | A | 3/1988 | Kumbrant |
| 5,515,739 | A | 5/1996 | Baerts |
| 5,591,894 | A | 1/1997 | Falk et al. |
| 5,979,253 | A | 11/1999 | Knevels et al. |
| 6,370,973 | B1 | 4/2002 | Wunsch et al. |
| 9,128,013 | B2 | 9/2015 | Song et al. |
| 2002/0067155 | A1 | 6/2002 | Conti et al. |
| 2003/0086473 | A1 | 5/2003 | Popelar et al. |
| 2004/0201371 | A1 | 10/2004 | Conti |
| 2010/0122590 | A1 | 5/2010 | Knevels |
| 2012/0293798 | A1 | 11/2012 | Song et al. |
| 2014/0318276 | A1 | 10/2014 | Cappa et al. |

FOREIGN PATENT DOCUMENTS

| | | | |
|---|---|---|---|
| DE | 32 00 010 A1 | 7/1983 | |
| DE | 197 31 830 C1 | 12/1998 | |
| DE | 299 09 595 U1 | 10/1999 | |
| DE | 10201023 B4 | 7/2004 | |
| DE | 10 2008 031 390 B4 | 4/2009 | |
| DE | 10 2011 121 183 A1 | 11/2012 | |
| EP | 0 556 474 A1 | 8/1993 | |
| EP | 2203732 B1 * | 3/2011 | ............... C21B 7/24 |
| EP | 2 397 834 A2 | 12/2011 | |
| EP | 2 525 207 A2 | 11/2012 | |
| GB | 1 528 922 A | 10/1978 | |
| WO | 2009030206 A2 | 3/2009 | |

OTHER PUBLICATIONS

EP Search Report dated Oct. 23, 2014 in EP Application No. EP14161157.
Office Action dated Aug. 24, 2015 in KR App No. 10-2014-0051336.
Office Action dated Feb. 14, 2016 in CN Application No. 201410108416.5.
Office Action dated May 5, 2016 in AU Application No. 2015-200292.
Office Action dated Sep. 16, 2016 in U.S. Appl. No. 14/264,658 by Cappa.
Office Action dated Dec. 20, 2016 in UA Application No. 201404631.
Office Action dated Nov. 18, 2016 in KR Application No. 10-2016-0008223.

* cited by examiner

SAMPLER AND SAMPLING METHOD FOR MOLTEN MATERIAL

CROSS-REFERENCE TO RELATED APPLICATIONS

This application is a Divisional of co-pending U.S. patent application Ser. No. 14/264,658, filed Apr. 29, 2014, the disclosure of which is incorporated herein by reference.

BACKGROUND OF THE INVENTION

The invention relates to a sampler having a sample chamber for a sample forming from a molten material, preferably for a sample forming from a molten metal, in particular from molten crude iron or molten steel. The sampler comprises at least one lower cooling body, at least one upper cooling body, at least one inner cooling body, and at least one filling part, preferably one filling tube, wherein the sample chamber is surrounded jointly at least by the lower cooling body and the inner cooling body, preferably is surrounded directly jointly, such that at least the sample chamber can be cooled by at least the lower and inner cooling bodies, wherein the filling part connected to the sample chamber merges into the sample chamber by a filling opening, and wherein the cooling bodies each comprise an outer surface.

Moreover, the invention relates to a method for sampling from a molten material having a melting temperature of more than 600° C., in particular a molten metal, preferably molten crude iron or molten steel, wherein the sampler is positioned at one end of a lance and/or carrier part, preferably of a carrier tube, and is immersed into the molten material, whereby the sample chamber of the sampler subsequently gets filled with molten material, and wherein then at least the sample is pulled out of the molten material by the sampler.

The invention also relates to a sample holder for accommodating a sampler, wherein the sample holder comprises a contact part for accommodating the sampler, and wherein at least one feed line for supplying gas via the contact part into the sampler, at least one discharge line for drawing off gas via the contact part from the sampler, and at least one gas line, which extends through the contact part and is connected to the sample chamber, are arranged in the sample holder.

The invention also relates to a device for implementing sampling processes in molten metals using a lance, in particular in molten steel using a sub-lance, wherein the lance comprises a lance body.

Moreover, the invention relates to a method for sampling from a molten material having a melting temperature of more than 600° C., in particular a molten metal, preferably molten crude iron or molten steel, wherein the sampler is positioned at one end of a lance and/or carrier part, preferably of a carrier tube, and is immersed into the molten material, wherein a sample holder is positioned between sampler and lance and/or carrier part, whereby the sample chamber of the sampler subsequently gets filled with molten material, and wherein then at least the sample is pulled out of the molten material by the sampler.

According to the prior art known to date, it is feasible to take samples out of a molten material, for example a molten metal.

For example, a measuring probe for measuring and sampling in a molten metal and having a measuring head arranged on a lance is known from European patent application Publication EP 2 397 834 A2, wherein the measuring head bears at least one temperature sensor and a sample chamber, wherein the sample chamber is surrounded, at least in part, by the measuring head and comprises a filling channel that extends through the measuring head. The filling tube, for example, is a quartz glass tube.

A sampler, in which the sample is generated by immersion into a bath of molten material is known from U.S. Pat. No. 3,646,816. In this context, sample chambers differing in shape are used to generate first a flat sample and second a needle-shaped sample, wherein an aluminum tube is used to prevent deoxidation in the entry region of the molten material entry tube. Openings are used to release the compressed air generated during taking the sample from the sampler. Metal discs are used in the region of the sample chambers to cool down the samples.

Moreover, German published patent application DE 32 00 010 A1 discloses the use of a lance for removal of metallic immersed samples for spectral analysis, wherein the end section of the lance that is immersed into the molten metal comprises an immersion ingot mold having a closed entry channel, wherein the immersion ingot mold is arranged in a protective gas atmosphere and the quantity of sample ascending through the filling channel compresses and/or displaces the protective gas. In this context, the lance comprises, in one embodiment, an overpressure valve and, in one embodiment, a valve for rinsing the immersion ingot mold with inert gas and for closing it in a gas-tight manner.

Moreover, it is known from German published patent application DE 10 2011 121 183 A1 to use, in a sampler, a cooling body made of copper that conducts heat well, such that rapid dissipation of heat from the sample that flowed into the cooling chamber proceeds such that the same is therefore cooled down rapidly, wherein the cooling body consists of two bodies that form the inner wall of the sample chamber arrangement. Moreover, it is also known from this document that the sample is surrounded by an inert gas at the time it is removed from the sample chamber.

One disadvantage of the prior art as known to date is that the molten material taken up into the sample chamber, which later forms the sample, cools down only very slowly in the sample chamber. Subsequent measurements on the cooled down sample can be made only after a long time interval to the true composition of the molten material, since the cool-down time is very long. Moreover, for example, oxidation reactions occur on the not yet cooled down sample due to the presence of ambient air, if the sample is removed from the sampler while it is still hot.

BRIEF SUMMARY OF THE INVENTION

It is therefore an object of the invention to devise a way in which the disadvantages described above can be reduced or overcome. Specifically, a way is to be devised for rapid and easy cooling of a sample taken up into a sample chamber, such that the solid sample arising during the cooling process can be removed from the molten material only a short time after taking up the molten material. Moreover, the sample should be prevented from reacting, for example with ambient air, by the cooling process being rapid.

It is another object of the invention to devise a way of filling the sample chamber with a molten material using simple technology and inexpensive means.

It is another object of the invention to create a method for sampling from a molten material, by which the sample formed from the molten material can be cooled down in a technologically easy manner and rapidly, for example for analysis thereof.

It is another object of the invention to create a method for sampling from a molten material by which the sample chamber can be filled rapidly.

The first object of the invention specified above is met in that the sampler comprises, between a region of the outer surface of the inner cooling body and the region of the outer surface of the upper cooling body opposite the outer surface of the inner cooling body, at least one gap for conducting at least one gas, preferably one inert gas, in particular argon or nitrogen, and in that the volume of the respective cooling body is larger than the volume of the gap, preferably by a ratio of at least 3:1, in particular at least 5:1, preferably at least 10:1, in particular at least 20:1, such that the sampler has better cooling performance.

The subsequent object is met in that the sampler has a switch arranged in it, which is connected to the feed line and the discharge line on the one hand and to the gas line on the other hand, and can be used to connect either the feed line or the discharge line to the gas line.

The object is also met in that a sample holder, as described below, can be connected to one end of the lance body and can have a sampler, as described below, connected to it, wherein the device comprises at least one feed line for supplying gas through the contact part into the sampler, at least one discharge line for drawing off gas through the contact part out of the sampler, and at least one gas line that extends in the sampler and is connected to the sample chamber.

The further object with respect to the method according to the first-mentioned invention is met in that at least one gas, preferably an inert gas, in particular argon or nitrogen, is supplied into the sampler before immersing it, whereby the gas flows out again from the sampler through at least one filling part, preferably a filling tube, and the sampler is subsequently immersed into the molten material, then the supply of gas is changed, in particular is interrupted or reversed in the direction of flow, followed by the sample chamber filling up with molten material, then gas being supplied again during or after the sample chamber fills with molten material, such that at least the sample chamber is cooled by the supplied gas.

The object with respect to the method for sampling according to the last-mentioned invention above is met in that at least one gas, preferably an inert gas, in particular argon or nitrogen, is supplied into the sampler, before immersing it, through at least one feed line and at least one gas line, whereby the gas flows out again from the sampler through at least one filling part, preferably a filling tube, and the sampler is subsequently immersed into the molten material. Then, the supply of gas is changed, in particular is interrupted or reversed in the direction of flow, by switching a switch in the sample holder from a position A to a position B, followed by the sample chamber filling up with molten material. Then, gas is supplied into the sampler again during or after the sample chamber fills with molten material by switching the switch from position B to position C, and at least the sample chamber is cooled by the supplied gas.

Moreover, the invention relates to a device for implementing sampling processes in molten metals using a lance, in particular in molten steels using a sub-lance, wherein the lance comprises a lance body, characterized in that a sample holder according to the invention can be arranged on one end of the lance body by a contact part for accommodating a sampler according to the invention. The device comprises at least one feed line for supplying gas through the contact part into the sampler, at least one discharge line for drawing off gas through the contact part out of the sampler, and at least one gas line that extends through the contact part and is connected to the sample chamber, wherein the switch is arranged in the lance body rather than in the sample holder.

Last, the invention relates to a device for producing a sample holder according to the invention, characterized in that the device comprises suitable means for producing the sample holder.

Moreover, the invention relates to a method for producing a sample holder according to the invention by a device according to the preceding embodiment.

In the scope of the invention, a change comprises the reduction, the switching off or the reversal. Reversal of the supply, i.e. reversing the direction of flow, generates a negative pressure in the sampler and thus in the sample chamber as well. The three states of change can just as well occur consecutively in combination.

It is feasible by the sampler according to the invention to cool down a sample formed from a molten material by the cooling bodies in a technologically easy and rapid manner to a temperature at which the sample can be removed from the sample chamber or, alternatively, can be used further in the sampler. Taking it out in terms of removing it can proceed by dropping or manipulating the sampler appropriately such that the sample is released upon destruction of the sampler. Moreover, the sampler enables cost-efficient cooling of the sample forming from the molten material.

The method according to the invention for sampling from a molten material can also be used to easily, inexpensively and rapidly cool a sample by the gas being re-supplied to the sampler. A cooled sample no longer reacts, for example, with ambient air or, alternatively, any reaction or change of the sample that does proceed is reduced by the cooling. Moreover, it is feasible, advantageously, that the sampler does not need any preparation for analysis of the solidified sample due to its dimension and the use of an inert gas, for example argon, in the sampler. Accordingly, no additional production machinery, such as a milling machine or polishing machine, is required at the factory building for processing of the removed sample. This has to be considered to be a particular advantage.

Moreover, it is feasible according to the invention to reduce or minimize the expenditure of time. There is neither a separate laboratory required, in which the sample is analyzed with possible prioritization issues, nor the use of a pneumatic shipping system or a conveyor belt with attendant restrictions related to the use of the submission, since the sample can be analyzed directly on site using an analytical unit, for example next to the converter and the unit of the lance used in the factory building. This also has to be considered to be another particular advantage.

The sample holder according to the invention can also render it feasible to fill the sample chamber of the sampler with molten material in an easy, inexpensive and rapid manner. Moreover, it is feasible, advantageously, that the sampler according to the invention has a simple and inexpensive design. Moreover, the sampler according to the invention can be integrated easily into existing devices for sampling.

The filling part connected to the sample chamber, through which the molten material flows from the bath of molten material into the sample chamber, is provided, for example, from a quartz glass, a ceramic material or the like.

The lower, upper and/or inner cooling body is advantageously designed to be of metal or a metal alloy, for example a steel alloy, which preferably has a higher melting point than the molten material forming the later sample in the sample chamber.

Moreover, alternatively or in addition, the cooling body can be coated. This allows, for example, an oxidation and/or a micro-structural change of the sample while the sample is cooling to be prevented, wherein the respective outside of the sample preferably is situated adjacent to the corresponding coated cooling body.

According to another advantageous embodiment of the sampler, at least the lower cooling body and the inner cooling body form a wall of the sample chamber, wherein the wall is formed by a region of the respective outer surface of the lower cooling body and of the inner cooling body, such that a sample chamber having a hollow space is formed between lower cooling body and inner cooling body.

Since the sample is situated between the lower cooling body and the inner cooling body while it is cooling down, it is feasible according to the invention to cool the sample in a manner that is particularly easy and rapid. This is the case, since the corresponding surface of the lower cooling body and of the inner cooling body preferably borders directly on the sample, such that heat can be dissipated directly by the respective cooling body and is then conducted out of the sampler by the flowing gas.

Another advantageous embodiment of the sampler has the sampler comprise at least one connector for supplying gas, preferably of an inert gas, in particular argon or nitrogen. The connector is also referred to as hybrid connector. The connector can be used to dissipate the heat transferred from the sample to the corresponding cooling body, in particular the lower and the inner cooling bodies, by a gas that is supplied through the connector. It is feasible in this context to adjust the quantity of supplied gas to the cooling effect desired in the individual case. It is preferred to use an inert gas, in particular argon or nitrogen, such that no reaction of the sample and the supplied gas proceeds. Another preferred object of the gas supplied through the connector is to keep the sample chamber free from molten material until the molten material is taken up into the same by having gas flow out of the filling part of the sampler into the molten material, such that no molten material can initially ingress into the sampler.

According to another advantageous embodiment of the sampler, at least the lower and the inner cooling bodies can be detached from each other. Due to this arrangement, the sample is easy to remove from the sample chamber, which preferably is formed between the lower cooling body and the inner cooling body. According to an embodiment of the invention, the cooled down sample and the lower cooling body cannot be detached from each other in this context while the cooled down sample is removed.

Having the gap, it is feasible, on the one hand, to let a certain amount of gas flow into the sampler. On the other hand, it is thus feasible to dissipate a major amount of heat that is generated in the sampler, for example after the molten material is taken up into the sample chamber. The shape of the gap in this context can be any three-dimensional geometrical shape, for example spherical, ellipsoidal, conical, trapezoidal, and/or any combination thereof. Alternatively or in addition, a free-form surface comprising different shapes in the gap is feasible just as well.

According to another advantageous embodiment of the sampler, the sampler comprises at least one gas exit opening for discharge of the supplied gas. According to the explanation provided above, it is feasible that supplied gas flows out of the filling part into the molten material before the molten material is taken up into the sample chamber. After molten material flows through the filling part into the sample chamber, the path is at least impaired or obstructed, such that gas supplied in the same quantities as before filling the molten material into the sampler in order to cool it needs to be discharged by other routes in order to prevent the pressure from increasing. This purpose is served by a gas exit opening, which enables a continued supply of gas for cooling, in particular after the molten material is taken up, for example through the gap between the cooling bodies, and then guides the gas to exit from the sampler without having to flow through the sample chamber.

According to another advantageous embodiment of the sampler, at least one of the cooling bodies, preferably the upper cooling body, comprises at least one ventilation opening. Having the ventilation opening in the region of the cooling body is advantageous in that the amount of gas that is supplied to the sampler and is used for cooling can be guided through the ventilation opening to the gas exit opening after sampling.

According to another advantageous embodiment, the ventilation opening can be closed by at least one closure, preferably a membrane, which can be opened, wherein the closure opens while or after the sample chamber is being filled with the molten material. According to the explanation provided above, the invention provides for conducting gas first through the cooling bodies, then through the sample chamber, and last out of the filling part until the molten material is taken up into the sample chamber. After filling the sample chamber with molten material, the path of flow of the gas is obstructed by the filling part either in part or, in particular, completely, such that gas required for cooling can then be conducted as before, through a closure, which can be opened, to exit from the sampler. In this context, the closure opens while or after the sample chamber is being filled with the molten material. In this context, the opening can be generated by a pressure increase in that the closure opens only from a certain pressure. Alternatively or in addition, it is feasible that the closure is influenced by the amount of heat of the molten material surrounding the sampler after the sampler is immersed into the hot liquid molten material to effect a switch from the state of the closure being closed to the closure being open.

The ventilation opening can, for example, have a round or angular shape or any combination of both, for example a round shape with straight segments, an ellipsoidal shape with angular segments or the like.

According to a further advantageous embodiment, the diameter of the ventilation opening is approx. 0.7 mm to approx. 1.3 mm, preferably 1.0 mm.

According to another advantageous embodiment of the sampler, the closure, preferably the membrane, comprises at least one plastic connection, preferably an adhesive tape, a hot melt adhesive, a PVC plastic stopper, a closure valve having a hot melt connector made of plastic material or the like. It is feasible that the heat of the molten material in the sample chamber melts the closure consisting of plastic material and thus deforms or dissolves it, such that the closure opens partly or completely. For this purpose, supplied gas can continue to flow through the sampler according to the explanations provided above in a predetermined and/or required quantity for cooling. Alternatively or in addition, it is feasible to open the closure consisting of a plastic connection by the influence of pressure generated by the quantity of supplied gas, for example by deformation of the closure.

After change of the properties of the closure, the supplied gas will then, for example, flow out of the ventilation opening or then out of the gas exit opening.

According to another advantageous embodiment of the sampler, the closure, preferably the membrane, has a pressure resistance of approx. 0.5 bar to approx. 4 bar, in particular between 1.7 bar and approx. 2.3 bar, preferably approx. 2.0 bar. Accordingly, it is feasible to have the closure open only from a certain pressure. A high pressure in the region of the closure can be generated by supplying a large amount of gas, for example at the point in time at which particularly strong cooling is required.

According to another advantageous embodiment of the sampler, the temperature resistance of the closure, preferably of the membrane, is approx. 50° C. to approx. 90° C., preferably approx. 70° C. This ensures that the closure does not open yet during the passage through the slag, which usually is situated on the molten material when the sampler is immersed. Temperature resistance being evident also leads to the closure not opening when it is exposed to ambient air, etc. When the sampler is immersed into the molten material, there is a time-delayed increase of the temperature in the region of the closure, such that a temperature of approx. 70° C. is established with a slight delay at the same, for example when the sampler has already been removed from the molten material.

According to a particularly preferred embodiment, the closure is designed as a membrane that allows only a certain amount of gas to pass. In this context, the amount can be a function, for example, of pressure and/or ambient temperature about the membrane, in particular with a focus on the quantity of heat and amount of gas supplied to the sampler.

According to another advantageous embodiment of the invention, the sampler comprises at least one measuring system, preferably a temperature sensor, in particular a thermocouple, for determining the position of the sampler in the molten material. Hereby, the supply of gas into the sampler can be controlled in each individual case. Alternatively or in addition, this enables optimal determination of the point in time of entry of the molten material through, for example, the filling tube into the sample chamber. A slag cap melts at a certain temperature (e.g. at 1,000° C.), and a gas flow in the sampler can be switched appropriately, such that molten material flows into the sample chamber and a sample is taken.

Alternatively, it is feasible that a lance according to the invention comprises a measuring system, preferably an inductive measuring system, wherein the sampler is positioned on the lance, preferably is affixed to the lance. A sample holder acting as a connection element can be arranged between the lance and the sampler. It is feasible to determine the position of the sampler in the molten material by the inductive measuring system. It is thus feasible to detect and at least measure the transition from slag to molten material, such that the gas supply can be changed during or after detection of the transition. Accordingly, it is also feasible to change the supply of gas into the sampler once the sampler has been immersed from the slag into the molten material. The inductive measuring system preferably comprises a wire coil, preferably for measuring the induction occurring upon the transition from slag to molten material.

According to another advantageous embodiment, the gap and the supply of gas allow the sample formed from the molten material to be cooled down in the sample chamber to a temperature of approx. 90° C. to approx. 200° C., preferably approx. 150° C. According to explanations provided above, it is preferred to conduct the gas through a gap between the corresponding cooling bodies, which enables rapid and easy cooling from the melting temperature to desired temperatures, for example 150° C. or less.

According to another advantageous embodiment, the filling part can be covered, at least by a protective cap, preferably by a protective cap made of metal. This enables particularly easy and gentle introduction of the sampler into the molten material, since the same is covered by the protective cap, which melts only after entry, for example through the slag and then into the molten material. Accordingly, the filling part for taking up the molten material into the sample chamber is exposed in the molten material only after the protective cap melts. However, according to the invention, gas is still being conducted out of the filling part within the molten material before the molten material enters into the sample chamber.

According to another advantageous embodiment, the sampler can be positioned on a lance and/or on a carrier part, preferably on a carrier tube, in particular on a sample holder and a carrier tube, in particular a carrier tube made of cardboard. This enables the sampler to be introduced into the molten material both manually and automatically. It is thus feasible, in particular, to position the sampler anywhere in the molten material. It is also feasible hereby to reuse the lance by using a carrier tube, which is damaged to the extent that it can no longer be used after uptake of the molten material and cooling down of the molten material in the sample chamber to form a sample.

In this context, the sample holder is protected by the carrier tube. Accordingly, the carrier tube is a disposable article that is used just once, in particular in order to protect the multiple-use lance. It is feasible, for example, to position a carrier tube of a certain length on a lance or a sample holder and to thus generate a certain distance between lance and sampler when the carrier tube takes up the sampler on its end opposite from the lance. The sample holder, which preferably connects the sampler and the lance, is preferably situated within the carrier tube. The carrier tube and the sampler are introduced appropriately into the molten material, such that they are contacting the molten material directly. In this context, the sample holder is protected by the carrier tube. The lance is also protected from the molten material.

In this context, it is feasible according to the invention to design the corresponding cooling body to have any of various geometries. It is feasible, for example, to design the inner cooling body to be of rectangular shape, square shape, disc shape, triangular shape, pyramidal shape, conical shape, spherical shape, circular shape or the like, for example a combination of the aforementioned. Referring, in particular, to the two-dimensional geometrical shapes, such as triangle, rectangle, circle, square or the like, the inner cooling body also comprises a certain thickness such that this results in a three-dimensional design of the cooling body. According to the invention, it is particularly preferred in this context for the shapes of the lower cooling body and of the upper cooling body to be adapted to the shape of the inner cooling body, such that this results in optimal cooling by gaps forming in the region of the sample chamber and sampler.

Alternatively or in addition, it is also feasible that the shape of the lower or upper cooling body has an influence on the shaping of the inner cooling body. The shape of the cooling body can be used to influence the shape of the gap (or vice versa).

The invention further provides for adapting the diameter or the dimensions of the gap according to the invention, which is particularly preferred to extend between the upper cooling body and the inner cooling body, to the amounts of gas needed. A gap shall be understood in this context to be a two-dimensional design, for example a conical gap that surrounds the surface of a corresponding conical inner cooling body. Optimal cooling of the cooling bodies and thus of the sample chamber and ultimately of the sampler is thus made feasible.

In the method according to the invention, it is preferred to supply the gas through the connector for the supply of gas to the sampler. Preferably, the connector is situated within the sample holder. As a result, gas can be supplied into the sampler in an easy and inexpensive manner. It is thus feasible, in particular, to connect various gases, which each are adapted to the molten material, to a connector of the type. It is feasible, for example, to connect gas A to the connector for molten material A and to connect gas B or the gas mixture B' for molten material B to the same connector.

Preferably, the gas flows through at least one gap between at least the inner cooling body and upper cooling body. According to explanations provided above, this facilitates optimal and rapid cooling of the initially liquid molten material in the sample chamber in order to generate a useful sample. Accordingly, the rapidly cooled sample can be removed from the sample chamber without any external influences, such as oxidation reactions, acting on the sample after removal of the sample from the sampler.

Preferably, the gas flows only out of the filling part, before the molten material is filled in, and flows out through at least one ventilation opening while or after the molten material is filled into the sample chamber. According to explanations provided above, it is feasible in this context to prevent parts of molten material or slag from entering into the sample chamber before the molten material is actually desired to flow into the sample chamber. Moreover, the presence of the ventilation opening prevents an overpressure from being built-up in the sampler, which would have an influence on the formation of the liquid or partly solidified sample, since any critical pressure that is generated is released by the gas flowing out of the ventilation opening.

Preferably, the gas flowing out of the ventilation opening is discharged through at least one gas exit opening for discharging the supplied gas from the sampler. The gas flowing out of the ventilation opening is discharged through the gas exit opening that is situated, for example, in the direction of the lance. Accordingly, it can be discharged from the sampler against the inflow direction of the gas.

Preferably, the closure, preferably the membrane, becomes permeable to gas or is destroyed while or after the molten material is filled into the sample chamber, due to the effect of the temperature of the molten material and/or the pressure of the supplied gas. It is thus feasible to regulate the gas flow flowing into the sampler appropriately, such that a certain amount of gas can be supplied.

Preferably, the gas flows out of the filling part after the protective cap, preferably the protective cap made of metal, has melted. According to explanations provided above, it is thus feasible to influence the time at which the molten material enters into the sample chamber.

Preferably, after filling the molten material into the sample chamber, the newly supplied gas flows through the gap, and then the gas preferably flows through the ventilation opening out of the sampler, whereby this cools down the temperature of the sample, preferably to a temperature of approx. 90° C. to approx. 200° C., in particular approx. 150° C. Hereby, and referring to the explanations provided above, rapid and simple cooling of the sample chamber and thus of the molten material or already solidified sample present therein is made feasible. At a temperature of approx. 150° C., for example, subsequent analysis or mechanical, chemical and/or electrical processing of the sample is made feasible, either after the sample has been removed from the sample chamber or while it is still present in the sample chamber. At 150° C. the sample can be removed easily, for example, by destroying the sampler without having to expect further critical reactions to occur due, for example, to ambient air.

Preferably, the sample is held by the lower cooling body. Moreover, alternatively or in addition, it is preferred that the inner cooling body is held by the upper cooling body.

It is preferable to use a measuring system, preferably a temperature measuring system, preferably a temperature sensor, in particular a thermocouple, or an inductive measuring system to regulate the supply of gas into the sampler, in particular it is preferred to change the supply of gas for filling the molten material into the sample chamber. Using the measuring system, it is therefore feasible to regulate the point in time at which the molten material flows into the sampler and thus into the sample chamber for the individual application on hand by using the measuring system to detect a condition at which an inflow of the molten material is desired to proceed. Moreover, negative influences, such as penetration through the slag in the direction of the molten material to be measured, can be reduced by the measuring system or, preferably, can even be eliminated according to the invention.

Preferably, the sample is supplied to an analytical facility while it is in the sampler. It is particularly preferred to remove the sample from the sampler in this context, i.e. from the sample chamber formed between the inner cooling body and the lower cooling body, and to then analyze it in a suitable device, for example in an optical emission spectrometer. In this context, the lower cooling body remains attached to the sample during removal of the sample in a preferred embodiment.

In an advantageous embodiment of the sample holder according to the invention, the sample holder comprises at least one gas exit opening, wherein the discharge line ends in the gas exit opening.

In another advantageous embodiment, the sample holder comprises at least one intermediate filter between switch and gas exit opening in the discharge line. Preferably, the intermediate filter is designed in the form of a gas filter.

In an alternative, advantageous embodiment of the sample holder, the feed line comprises at least one feed valve and/or the discharge line comprises at least one Venturi nozzle.

In another advantageous embodiment, the discharge line comprises at least one opening, preferably one opening in the region of the Venturi nozzle.

In an alternative, advantageous embodiment of the sample holder, a part of the discharge line connected to the switch arranged in the sample holder has a larger diameter than the other parts of the discharge line, forming at least one vacuum chamber that comprises at least one gas suction line for connection to at least one vacuum pump.

In an alternative, advantageous embodiment of the sample holder, a part of the discharge line connected to the switch arranged in the sample holder merges into a hollow internal space of the sample holder, wherein the internal space comprises a gas-tight wall with at least one gas suction line for connection to at least one vacuum pump.

In another advantageous embodiment, the vacuum chamber has a volume from 0.1 l to approx. 0.5 l, preferably approx. 0.3 l.

In another advantageous embodiment, the sample holder and the contact part each have a cross-section with an axially symmetrical circumference, in particular a circular circumference.

In a preferred embodiment of the sample holders according to the invention, at least one gas filter is arranged between the gas line connected to the sample chamber and the switch.

In a preferred embodiment of the sample holders according to the invention, the sample holder comprises at least one hybrid contact part, and the sampler comprises at least one hybrid connector. The contact part is also referred to as a contact block.

Preferably, the hybrid contact part is made of a metallic material and the hybrid connector is preferably made of plastic material. Due to the properties of the hybrid contact part and the, preferably corresponding, hybrid connector, electrical signals as well as pneumatic signals can be conducted simultaneously or with a time delay by the respective hybrid component, i.e. a dual, i.e. a hybrid, function is feasible. The hybrid contact part can comprise, in addition, a hybrid unit through which the at least one gas line and at least one cable are guided.

In the device for implementing sampling processes, a preferred embodiment of the sample holder has a length measured in axial direction, from the end of the contact part to the opposite side of the sample holder and the switch is arranged at a distance of at most 0.3× length, in particular 0.1× length, from the end of the contact part.

In the corresponding device according to the invention for implementing sampling processes, in a preferred embodiment, sampler and sample holder can be connected by a carrier part, preferably a carrier tube, in particular a carrier tube made of cardboard. In this context, the sampler itself can just as well be connected to the sample holder.

In a variant of the method according to the invention for sampling from a molten material, with the switch being in position B, at least an amount of gas that is present at least in the sample chamber and the filling part flows by the sample holder according to the invention in the direction of the sample holder due to the supply of gas in the feed line being interrupted by the switch.

In a further, alternative embodiment of the method, with the switch being in position B, it is preferred that at least an amount of gas that is present at least in the sample chamber and the filling part is drawn in by the sample holder according to the invention in the direction of the sample holder due to the gas already supplied being reversed in direction by the Venturi nozzle, such that the supplied gas is drawn off.

In a further, alternative embodiment of the method, with the switch being in position B, at least an amount of gas that is present at least in the sample chamber and the filling part is drawn in by the sample holder according to the invention in the direction of the sample holder by the gas already supplied being reversed in direction by the negative pressure in the vacuum chamber, such that the supplied gas is drawn off.

In a further, alternative embodiment of the method, with the switch being in position B, it is preferred that at least an amount of gas present at least in the sample chamber and the filling part is drawn in by the sample holder according to the invention in the direction of the sample holder by the gas already supplied being reversed in direction by the negative pressure in the vacuum chamber, such that the supplied gas is drawn off.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
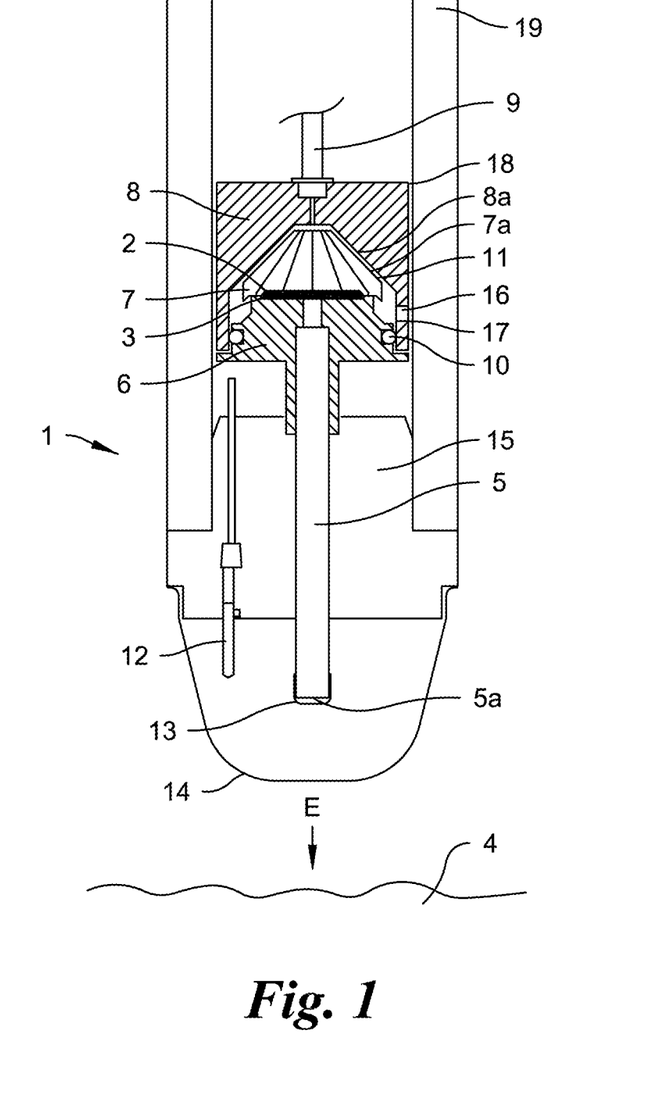
FIG. 1 is a schematic, longitudinal sectional view of a sampler according to a particularly preferred embodiment of the invention.

FIG. 1 shows a sampler 1 that had been immersed into a liquid and hot bath of molten material for the purpose of sampling.

The sampler 1 comprises a sample chamber 2. A sample 3 is shown in exemplary manner in the sample chamber 2 shown in FIG. 1 and has been formed from a molten material, from molten steel 4 in the present exemplary embodiment. The molten steel 4 has a temperature of above 600° C. and is shown as a detail in exemplary manner in FIG. 1.

The sampler 1 further comprises a filling tube 5 that comprises a filling opening 5a and a through-going hole. The filling tube 5 consists of quartz glass in the present exemplary embodiment. At the end facing the sampler, the filling tube 5 merges into the sample chamber 2 and is connected to the sample chamber 2.

According to FIG. 1, the sampler 1 comprises three cooling bodies in the present exemplary embodiment, namely a lower cooling body 6, an upper cooling body 8, and an inner cooling body 7. According to the present exemplary embodiment, the sample chamber 2 is surrounded directly by the lower cooling body 6 and the inner cooling body 7. The lower cooling body 6 and the inner cooling body 7 thus surround the sample chamber 2 directly and form the inner wall of the sample chamber 2. Accordingly, the inner wall is formed by the two cooling bodies 6, 7, since their outer surfaces form a wall of the sample chamber 2. The wall is referred to as inner wall according to the invention. Accordingly, by the inner wall, the sample chamber is considered to be a closed space into which molten material can flow. According to the invention, the sample chamber 2 can be cooled by the cooling bodies 6, 7, 8.

According to FIG. 1, the sampler 1 comprises at least one connector 9 for the supply of gas or a gas mixture into the sampler 1. The connector 9 is also referred to as hybrid connector. An inert gas, for example argon, is supplied through the connector 9 into the sampler 1 in the present exemplary embodiment.

According to FIG. 1, the inner cooling body 7 is shaped like a cone, wherein the outer surfaces of the inner cooling body 7 form trapezoidal surfaces. The upper cooling body 8 is adapted to the shape of the inner cooling body, such that it forms a corresponding negative shape according to FIG. 1. The inner cooling body 7 is held by the upper cooling body 8 in the context of the present exemplary embodiment. The lower cooling body is adapted to the shape of the upper cooling body 8 and of the inner cooling body 7 in appropriate manner, such that the upper cooling body and the lower cooling body 6 form a tight connection at their contact surfaces. The contact surfaces of the lower cooling body 6 and upper cooling body 8 have a circumferential O-ring 10 situated in a groove of the lower cooling body 6 in the present exemplary embodiment to provide for tightness, in particular pressure- and gas-tightness.

According to explanations provided above, the sample 3 is situated in the sample chamber 2 between the inner cooling body 7 and the lower cooling body 6. According to the invention, the sample 3 is held in place by the lower cooling body 6. According to FIG. 1, at least the lower cooling body 6 and the inner cooling body 7 can be detached from each other such that the sample 3 can be removed from the sampler 1. According to the present exemplary embodiment, the cooled down sample 3 remains firmly connected to the lower cooling body 6 in this context, while the sample 3 is removed.

According to FIG. 1, the sampler 1 comprises, between an outer wall 7a of the inner cooling body 7 and the outer wall 8a of the upper cooling body 8 situated opposite from the outer wall 7a of the inner cooling body 7, at least one gap 11 for the supply of the inert gas used in the present exemplary embodiment. Accordingly, a three-dimensional gap 11 is present between the two corresponding cooling bodies 7, 8.

In this context, the gap 11 extends between the two outer walls 7a, 8a, such that a conical gap 11 is formed in the sampler 1. By the gap 11 shown in FIG. 1 and by the supply of inert gas, the sample 3 formed from the molten steel 4 in the sample chamber 2 in the present exemplary embodiment can be cooled to a temperature of approx. 150° C. both rapidly and easily.

The volume of the corresponding cooling bodies 6, 7, 8 is larger than the volume of the gap 11 (according to FIG. 1), preferably the ratio of the volume of the corresponding cooling bodies 6, 7, 8 and the volume of the gap 11 is at least 20:1. This provides for better cooling performance of the sampler 1 according to FIG. 1.

In the present exemplary embodiment, the sampler 1 further comprises a measuring system, a thermocouple 12 in the present exemplary embodiment, by which the temperature and thus the position of the sampler 1 in the warm molten steel 4 can be determined.

According to explanations provided above, the sampler 1 in the exemplary embodiment shown in FIG. 1 has already been dipped into the molten steel 4 in order to generate a sample 3 and has been removed from same after generating the sample 3 in the sample chamber 2. In this context, the sample 3 is surrounded in the sample chamber 2 by the inner walls thereof. Accordingly, the cover 13 is shown by dashed lines in the region of the filling opening 5a of the filling tube 5, since it has melted in the molten steel 4. Moreover, the protective cap 14 used in the present exemplary embodiment is shown by dashed lines for the same reason. Both the cover 13 and the protective cap 14 have melted after the sampler 1 was immersed into the molten steel 4. Accordingly, the sampler 1 comprises a cover 13 and a protective cap 14 before it is immersed into the molten steel 4.

The sampler 1 further comprises a sand body 15 through which extends the filling tube 5 and in which the thermocouple 12 is situated. In this context, the sand body 15 has a closed shape like a block of sand. In this context, the filling tube 5 projects from the sand body 15 at a certain distance according to FIG. 1. The thermocouple 12 is in direct contact with the molten steel 4. The temperature measurement proceeds by the thermocouple 12 that is situated in the molten steel 4.

The upper cooling body 8 comprises a ventilation opening 16 in the exemplary embodiment according to FIG. 1. The ventilation opening 16 is closed by a membrane 17, which can be opened, in the present exemplary embodiment. According to FIG. 1, the membrane 17 is open for gas after the molten steel 4 flows into the sample chamber 2, wherein the membrane opened up at least upon the sample chamber 2 being filled with molten steel 4 in the present exemplary embodiment. The membrane 17 according to the exemplary embodiment shown in FIG. 1 is, for example, a hot-melt adhesive that is influenced by the heat of the molten material, such that the membrane 17 opens up. In the present exemplary embodiment, the ventilation opening 16 has a diameter of 1 mm, wherein the ventilation opening 16 takes the shape of a round hole. In the exemplary embodiment according to FIG. 1, the pressure resistance of the closed membrane 17 is approx. 2 bar and the temperature resistance of the membrane 17 is approx. 70° C. in the present exemplary embodiment.

Moreover, the sampler 1 in the present exemplary embodiment comprises a gas exit opening 18 for discharge of the supplied gas. With membrane 17 being open, the gas supplied to the sampler 1 flows out of the sampler 1 again through the gas exit opening 18.

Figure 3:
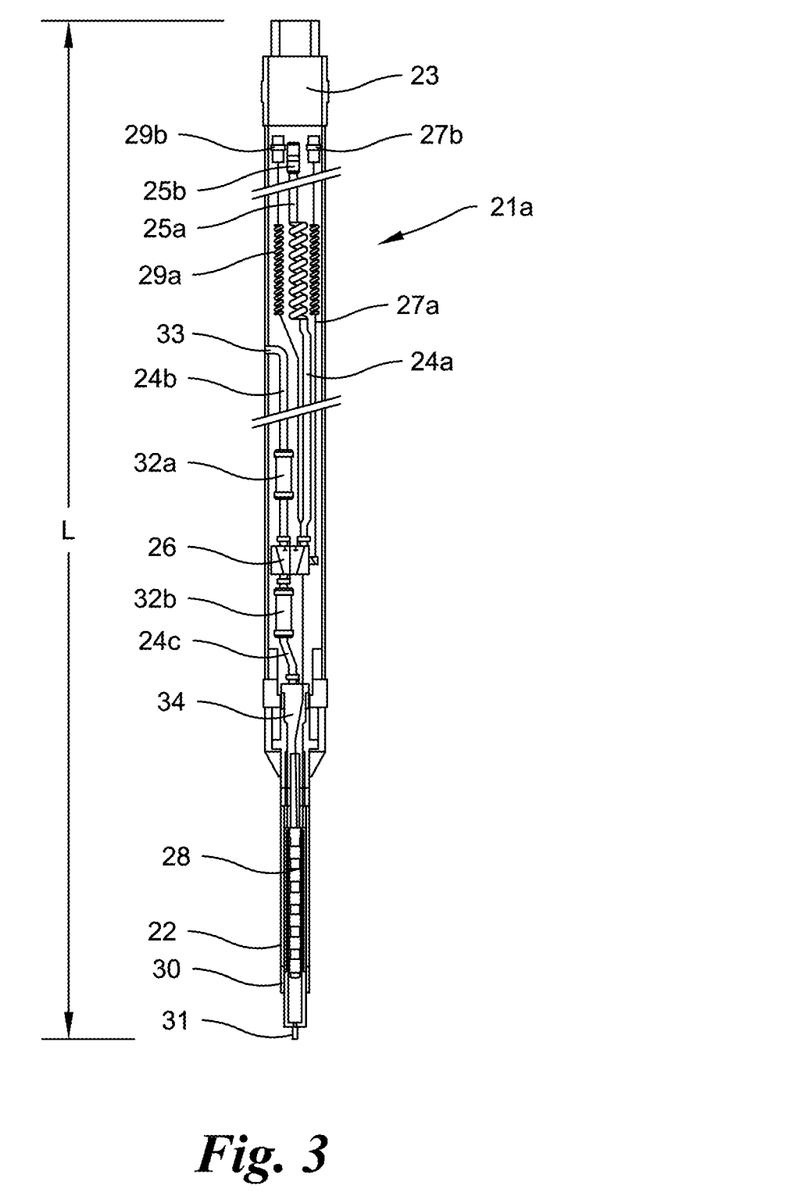
FIG. 3 is a schematic, longitudinal sectional view of a particularly preferred embodiment of a sample holder according to the invention.
Figure 4:
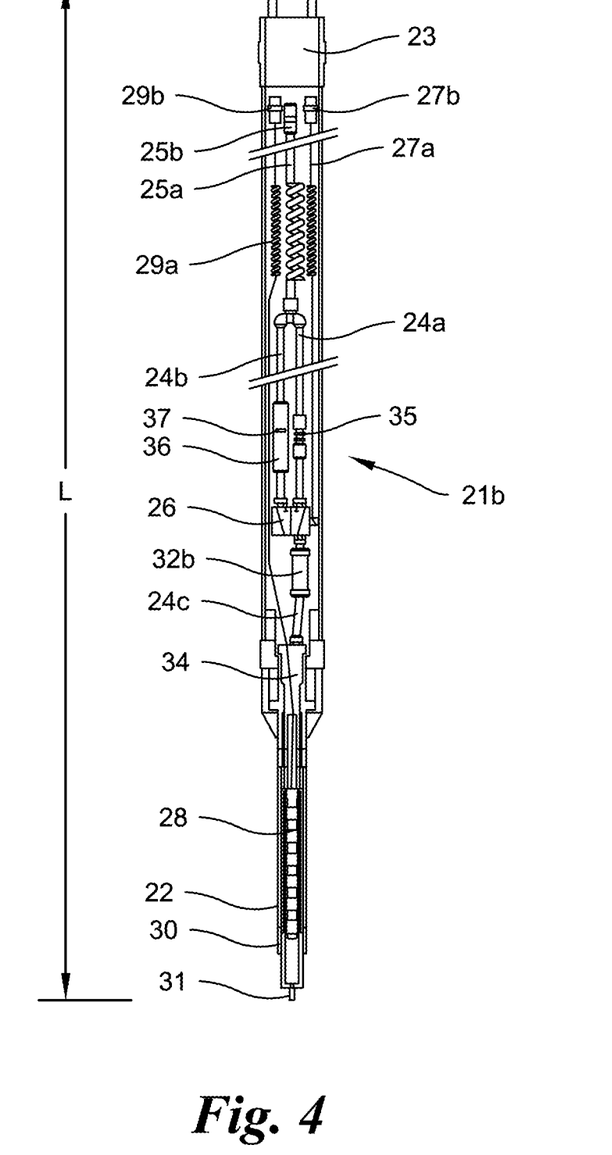
FIG. 4 is a similar view of an alternative embodiment of a sample holder according to the invention.
Figure 5:
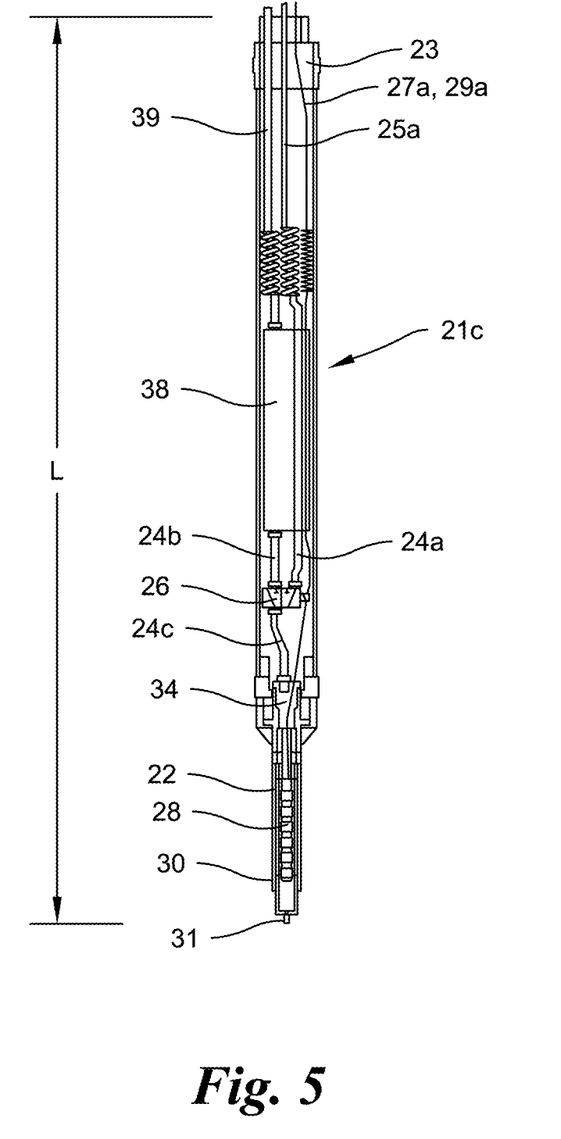
FIG. 5 is a similar view of another alternative embodiment of a sample holder according to the invention.

Moreover, FIG. 1 shows a carrier tube 19 made of cardboard. The sampler 1 is connected firmly to the carrier tube 19. The other region of the carrier tube 19 is affixed to a sample holder (not shown in FIG. 1) that is shown in exemplary manner in FIGS. 3 to 5 and is described in more detail in the following and is thus positioned for sampling from the molten steel 4. The sample holder according to embodiments of FIGS. 3 to 5 is therefore surrounded by the carrier tube 19 made of cardboard. The sampler 1 is therefore connected to the sample holder on one side of the corresponding sample holder.

According to FIG. 1, the three cooling bodies 6, 7, 8 are situated in the region of the carrier tube 19 in this context. In the exemplary embodiment according to FIG. 1, the sampler 1 is designed in particular for a sub-lance, such that the sampler 1 is used for a sub-lance and a corresponding device. In this context, it is preferable that the sub-lance in the form of a lance is affixed in the region of the connection of carrier tube 19 and sample holder.

A process of sampling according to the invention from the molten steel 4 by the sampler 1 according to FIG. 1 is described in exemplary manner in the following.

According to explanations provided above, the carrier tube 19 made of cardboard situated at the end of a lance (not shown here) positions the sampler 1 according to FIG. 1 also by a sample holder that is shown in FIGS. 3 to 5. The inert gas is supplied through the connector 9 into the sampler 1 before immersing the sampler 1 into the molten steel 4. The gas supplied through the connector 9 flows through the three-dimensional gap 11 along the outer walls 7a, 8a between inner cooling body 7 and upper cooling body 8, then through the empty sample chamber 2 into the filling tube 5, which is still closed by a cover 13 before immersion into the molten steel 4. Moreover, according to explanations provided above, the sampler 1 further comprises a protective cap 14 made of metal. Accordingly, the gas flows all the way into the filling tube 5. In this context, a pressure of maximally 2 bar is built-up in the sampler 1 in the present exemplary embodiment, such that the membrane 17 remains closed. Accordingly, the gas cannot flow through the ventilation opening 16, since the membrane 17 is still closed.

Subsequently, the sampler 1 is immersed into the molten steel 4 in immersion direction E. In this context, the sampler 1 is initially guided through the slag of the molten steel 4 and then into the molten steel 4 itself in the present exemplary embodiment. The position of the sampler 1 in the molten steel 4 is not shown in FIG. 1.

Due to the heat of the molten steel 4, the protective cap 14 and also the cover 13 melt subsequently. Protective cap 14 and cover 13 are made of metal. The gas supplied through the connector 9 thus flows out of the filling tube 5 out of the sampler 1 into the molten steel 4 in the direction of immersion direction E, upon which no molten steel 4 can ingress into the filling tube 5 however. The three cooling bodies 6, 7, 8 and the sample chamber 2 are situated above the sand body 15, i.e. these are arranged in the direction opposite from the immersion direction E. Accordingly, these are protected by the carrier tube 19 inside the bath of molten material, even after immersion into the molten steel 4.

The supply of gas into the sampler 1 is regulated by the temperature sensor in the form of the thermocouple 12, in that the temperature is measured by the thermocouple 12 in accordance with the explanations provided above. According to the exemplary embodiment shown in FIG. 1, the supply of gas in this context for subsequently filling molten steel 4 into the sample chamber 2 is interrupted by effecting a change while the sampler 1 is in a certain position in the molten steel 4, since the temperature of the molten steel 4 indicates the position of the sampler 1 in the molten steel 4.

In the process, the sand body 15 heats up as well. Once the position in the molten steel 4 is reached, the supply of gas is therefore changed briefly in the present exemplary embodiment, such that the sample chamber 2 can then fill up with molten steel 4. In the present exemplary embodiment, the supply of gas is changed in that the supply of gas is switched off. In this context, the molten steel 4 flows through the hole of the filling tube into the sample chamber 2, whereby the molten steel enters into the hole at the filling opening 5a.

Alternatively, it is feasible to generate a negative pressure inside the sample chamber 2 instead of switching off the supply of gas, such that the sample chamber 2 can fill up with molten steel 4 even more rapidly. A negative pressure can be generated, for example, by generating a negative pressure on the connector 9. Based on the design of the sampler 1 described above, the molten steel will then flow into the sample chamber 2 due to the suction effect of the negative pressure.

After the sample chamber 2 fills with molten steel, the sampler 1 is pulled out of the molten steel 4 using the lance and the carrier tube 19, such that the sampler 1 according to FIG. 1 is present with a filled sample chamber 2.

Due to the temperature of the molten steel 4, the membrane 17 becomes gas-permeable in the present exemplary embodiment while the molten steel 4 is filled into the sample chamber 2, since the heat radiation at the temperature of the molten steel 4 has an influence on the membrane 17 or heats the cooling bodies 6, 7, 8 to the extent that the membrane 17 is destroyed in the process. The membrane 17, which was closed before, has now opened up for gas.

Accordingly, it is feasible in the exemplary embodiment according to FIG. 1 to again supply gas into the sampler 1 after filling the sample chamber 2 with molten material 4 and after pulling the sample chamber 1 out of the molten steel 4, such that the sample 3 is cooled by the inert gas supplied. Accordingly, the supply of gas into the sampler 1 is switched on again afterwards in the present exemplary embodiment.

Since the sample 3 is still present in the sampler 1 and fills the sample chamber 2 and thus closes it, the inert gas flows through the connector 9 and then through the conical gap 11 about the inner cooling body 7 that borders on the sample 3 on one wall side. In this context, according to FIG. 1, the gas also flows about the lower cooling body 6 and the upper cooling body 8 due to the geometrical design of the gap 11, such that the same is also cooled in the process. Finally, the gas then flows out of the ventilation opening 16, such that the gas flowing out of the ventilation opening 16 is discharged through the gas exit opening 18 out of the sampler 1. It also flows through the gas-permeable membrane 17 in the region of the ventilation opening 16 in this context.

The newly supplied gas that takes up the heat of the sampler 1 and flows through the gap 11 leads to the temperature of the sample 3 being cooled down rapidly and easily, in the present exemplary embodiment to a temperature of approx. 150° C. Moreover, the dimensions of the respective cooling bodies 6, 7, 8 and the respective size ratio of cooling bodies 6, 7, 8 to the gap 11 lead to rapid dissipation of the heat.

At a temperature of approx. 150° C., it is easily feasible to remove the sample 3 from the sampler 1 and to pass it on, for example, to an analytical facility in the present exemplary embodiment. The analytical facility is not shown in FIG. 1.

Figure 2:
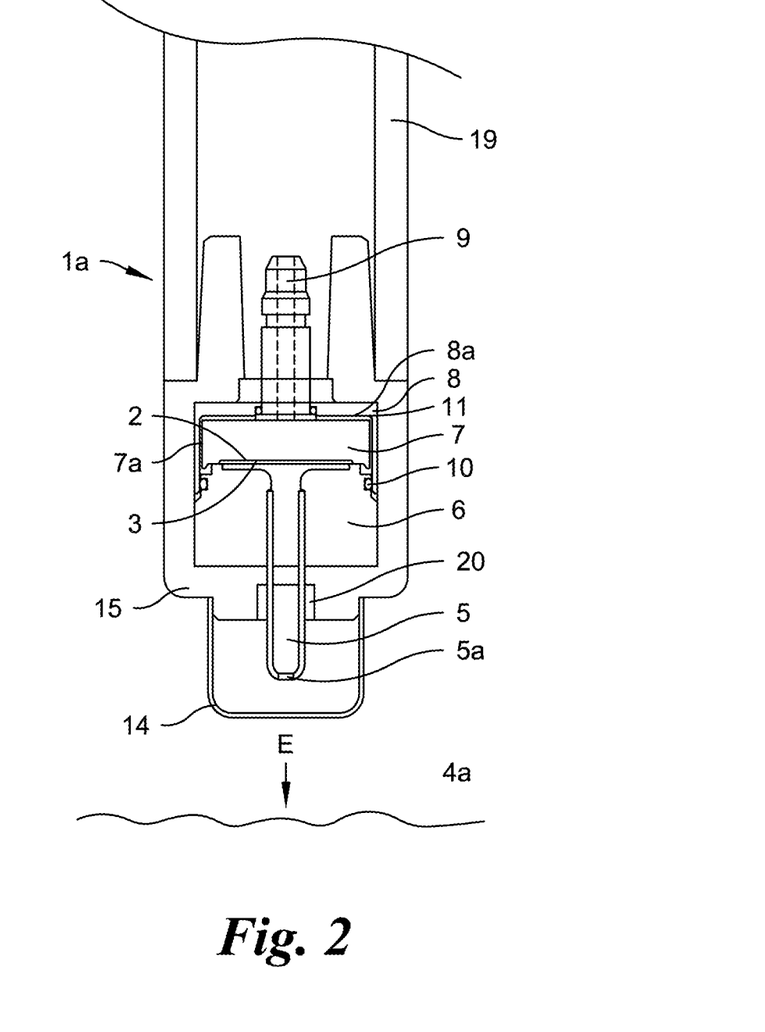
FIG. 2 is a similar view of an alternative embodiment of a sampler according to the invention.

FIG. 2 shows another, alternative exemplary embodiment of a sampler 1a. In particular, only the differences as compared to the sampler 1 shown in FIG. 1 are described.

Identical technical components are provided with the same reference numbers, whereas new components are provided with new reference numbers, wherein the geometrical shape of corresponding components might differ between FIG. 1 and FIG. 2.

FIG. 2 shows a sampler 1a having a sample chamber 2 and a sample 3 formed in the sample chamber 2 from a molten metal 4a that is shown in exemplary manner and as a detail.

Moreover, FIG. 2 shows the lower cooling body 6, the inner cooling body 7, and the upper cooling body 8 which the sampler 1a comprises. Moreover, according to FIG. 2, the sampler 1a comprises a connector 9 for the supply of inert gas as used in the present exemplary embodiment, in particular argon or nitrogen.

Moreover, the sampler 1a is firmly positioned on a carrier tube 19. Moreover, the sampler 1a has a sample holder (not shown in FIG. 2) positioned on it in an embodiment according to FIGS. 3 to 5, wherein the carrier tube 19 surrounds the sample holder. Moreover, the sampler 1a comprises a filling tube 5 which has a hole and consists of quartz glass or ceramic material. However, according to FIG. 2, the filling tube 5 does not comprise a cover.

The cooling bodies 6, 7, 8 and the sample chamber 2 and the sample 3 all are situated in a hollow sand body 15 of a different shape than in the exemplary embodiment according to FIG. 1. That is, the sand body 15 according to FIG. 2 surrounds the cooling bodies 6, 7, 8 in the form of a housing.

In this context, the filling tube 5 projects from the sand body 15 and is affixed partly with cement 20 in the region of the lead-through. The filling tube 5 projects somewhat from the hollow sand body 15 according to FIG. 2 in this context.

According to explanations provided above, the three cooling bodies 6, 7, 8 are situated inside the sand body 15. The lower cooling body 6 is designed to be larger in volume as compared to the inner cooling body 7 and the upper cooling body 8. The volume of the corresponding cooling body 6, 7, 8 relative to the volume of the gap 11 is at least larger than the volume of the gap 11, preferable the ratio formed is at least 20:1.

The inner cooling body 7 comprises a thick, circular disc shape and is enveloped in three dimensions of space by the upper cooling body 8. The geometrical design allows the upper cooling body 8 to additionally engage the lower cooling body 6 resulting in a closed connection between upper cooling body 8 and lower cooling body 6, in which the inner cooling body 7 itself is arranged.

For sealing the upper cooling body 8 to the lower cooling body 6, an O-ring 10 is arranged in the region of the contact surface in a groove of the lower cooling body 6. According to FIG. 2, a three-dimensional gap 11 in the form of a three-dimensional cup is provided between the upper cooling body 8 and the inner cooling body 7. Due to the O-ring seal and the geometry of the cooling bodies 6, 7, 8, this leads to the formation of a gas- and pressure-tight arrangement.

In this context, the inner cooling body 7 comprises an outer wall 7*a* that corresponds to the outer wall 8*a* of the upper cooling body 8 such that the gap 11 is formed that surrounds the entire inner cooling body in three dimensions of space.

Moreover, the position of the sampler 1*a* shown in FIG. 2 in the molten metal 4*a* is determined by a measuring system in the form of an inductive measuring system (not shown here). Using the inductive measuring system, it is feasible to measure and thus determine the position of the sampler 1*a* in the molten metal 4*a*. For this purpose, the inductive measuring system is situated in the lance, not shown here, in the present exemplary embodiment, wherein the measuring system is used to determine the position of the sampler 1*a* in the molten metal 4*a* when same is immersed, for example fully, in the molten metal 4*a*.

As described above referring to FIG. 1, FIG. 2 shows the sampler 1*a* after being pulled out of the molten metal 4*a*, wherein the sample 3 formed from the molten metal 4*a* is present in the sample chamber 2. Accordingly, the protective cap 14, which the sampler 1*a* comprises, is also shown by dashed lines, since it had already melted in the molten metal 4*a*. However, the sampler 1*a* comprised a protective cap 14 before it was immersed.

It is possible that the sampler 1*a* comprises a ventilation opening 16 and a gas exit opening 18. Neither of these is shown in FIG. 2.

The sampler 1*a* according to FIG. 2 is designed in the way of a sampler for molten crude iron (hot metal sampler).

To produce a sample 3 in the sample chamber 2 of the sampler 1*a* according to FIG. 2, the lance on which the carrier tube, the sample holder, and the sampler 1*a* are positioned, is introduced into the molten metal 4*a* in the immersion direction E. Once they are immersed, the sample holder and carrier tube surrounding it and the sampler 1*a* are situated fully in the warm bath of molten material.

Before immersion, an inert gas is supplied through the connector 9 into the sampler 1*a* according to explanations provided above. In this context, the gas flows through the gap 11, then through the sample chamber 2, in which no sample 3 is present yet, and lastly through the filling tube 5 in the direction of protective cap 14.

Once the sampler 1*a* is immersed into the molten metal 4*a*, the protective cap 14 melts, such that the supplied gas flows into the molten metal 4*a*. The position of the sampler 1*a* in the molten metal 4*a* is determined by the inductive measuring system such that, according to the invention, the supply of gas is stopped if the position is not the desired position.

It is also feasible, alternatively, to establish suction, due to a negative pressure, in reverse direction as compared to the flow direction of the inert gas described above such that a negative pressure is generated in the sample chamber 2 by which the molten metal 4*a* flows through the filling tube 5 into the sample chamber 2 and fills the same with molten metal 4*a* in a particularly easy and rapid manner.

After filling the sample chamber 2 with molten metal 4*a*, the sampler 1*a* is guided out of the molten metal 4*a* against the direction of entry E using the lance.

In the present exemplary embodiment, after the sampler 1*a* has been guided out of the molten metal 4*a* into the position according to FIG. 2, gas is supplied again through the connector 9 and the gap 11, such that the sampler 1*a* and the sample 3 are being cooled.

Subsequently, it is feasible to remove the solidified and cooled down sample 3 from the sampler 11*a*, since the lower cooling body 6 and the inner cooling body 7 can be detached from each other. In this context, the lower cooling body 6 and the cooled down sample 3 cannot be detached from each other according to the present exemplary embodiment.

Three embodiments of a sample holder are described in detail in the following. In this context, the sample holder is connected to a connector 9 of the corresponding sampler 1, 1*a*. According to explanations provided above, the sample holder is then surrounded by the cardboard tube in the form of the carrier tube 19, and the sample holder is connected to the corresponding lance on the side opposite to the side of the sampler 1, 1*a*. The cardboard tube therefore surrounds the sample holder and borders on the lance and on the sampler 1, 1*a*.

The supply of gas can be changed in order to fill the molten material into the sample chamber 2 by the three exemplary sample holders according to FIGS. 3 to 5. These each utilize different technologies to first conduct gas through the connector 9 of the sampler before the filling process and then to change the supply of gas in order to fill the sample chamber 2. This is described in detail in the following.

FIG. 3 shows a sample holder 21*a* for preferred accommodation of a sampler 1 that is shown in FIG. 1. For details of the design of the sampler 1 according to FIG. 1, please refer to the explanations provided above.

The sample holder 21*a* comprises a contact block 22 as a hybrid component for accommodating the sampler 1. According to FIG. 3, the contact block 22 is arranged on one end of the sample holder 21*a*. The contact block 22 corresponds to the hybrid connector, which is also referred to as connector 9 of the sampler 1, such that contact block 22 and hybrid connector can engage each other. An accommodation device 23 is arranged on the opposite side of the sample holder 21*a* and comprises a thread in the present exemplary embodiment.

Moreover, multiple gas lines are arranged in the sample holder 21*a*. In the exemplary embodiment according to FIG. 3, the sample holder 21*a* comprises a feed line 24*a*, a discharge line 24*b*, and a gas line 24*c*. In this context, the gas line 24c is also situated in contact block 22. It is feasible to supply gas through the feed line 24a via the contact block 22 into the sampler 1 (not shown in FIG. 3). In this context, connector 9 is used for supplying the gas. According to FIG. 3, the gas line 24c extends through the contact block 22 and is therefore connected to the sample chamber 2 (not shown in FIG. 3), when sampler 1 and sample holder 21a are connected to each other. Moreover, it is feasible, by discharge line 24b, to discharge gas via the contact block 22 out of the sampler 1 (not shown here). Furthermore, there is a gas connection 25b connected to feed line 24a present in the region of the one end of the sample holder 21a, i.e., according to FIG. 3, in the region of the accommodation device 23. According to FIG. 3, the gas connection 25b is connected to a gas feed line 25a.

Moreover, according to FIG. 3, the sample holder 21a comprises a switch 26, which is arranged in the sample holder 21a and is connected, on one side, to the feed line 24a and the discharge line 24b and, on the other side, to the gas line 24c. The change of the state of the switch 26 is implemented by the switching cable 27a, wherein a switching cable connection 27b to which a cable for switching can be connected is arranged on the end of the switching cable 27a in the region of the accommodation device 23 of the sample holder 21a. Moreover, the sample holder 21a comprises, in the region of the contact block 22, measuring contacts 28 that are arranged in the region of the contact block 22.

The measuring contacts 28 are connected by a signal cable 29a whose end is situated in the region of the accommodation device 23 whose end has a signal cable connector 29b arranged on it. Six measuring contacts 28 are arranged in series in the present exemplary embodiment according to FIG. 3.

Moreover, a seal 30 is arranged in the region of the contact block 22 such that a gas-tight connection between the sample holder 21a and the sampler 1 (not shown here) is feasible when the two components are connected. Accordingly, a gas-tight connection is established between connector 9 according to FIG. 1 and the contact block 22. According to FIG. 3, the contact block 22 further comprises a gas socket 31 through which the gas can flow in order to flow through the gas line 24c.

According to FIG. 3, the discharge line 24b is guided through a gas exit opening 33 to exit from the sample holder 21a. A gas filter 32a is arranged between the gas exit opening 33 and the switch 26 in the present exemplary embodiment. Another gas filter 32b is arranged in the region of the gas line 24c.

Moreover, the sample holder 21a comprises a hybrid unit 34 that is arranged between switch 26 and gas socket 31, whereby the hybrid unit 34 allows the gas line 24c and the signal line 29a to be connected directly and fixedly to the sampler 1 (not shown here). According to explanations provided above, the contact block 22 is plugged into the connector 9 in fitting and gas-tight manner for this purpose.

Accordingly, it is characteristic of the sample holder 21a shown in FIG. 3 that the sample holder 21a comprises the gas exit opening 33, whereby the discharge line 24b of the sample holder 21a ends in the gas exit opening 33. In this context, the gas filter 32a, in the form of an intermediate filter, is arranged between switch 26 and gas exit opening 33 of the discharge line 24b. According to FIG. 3, the sample holder 21a and the contact block 22 each have a cross-section with a circular circumference.

FIG. 4 shows an alternative embodiment of a sample holder 21b, whereby identical components are provided with the same reference numbers and new components are provided with new reference numbers in the following.

In the following, the description of FIG. 4 first describes the changes as compared to the sample holder 21a shown in FIG. 3. The sample holder 21b shown in FIG. 4 comprises no gas exit opening 33 and no gas filter 32a in the form of an intermediate filter. However, the sample holder 21b comprises a feed line 24a and a discharge line 24b that are connected to a single gas feed line 25a in the region of the sample holder 21b. According to FIG. 4, the feed line 24a and the discharge line 24b each are separately connected to a switch 26. A feed valve 35 is arranged in the feed line 24a and a Venturi nozzle 36 is arranged in the discharge line 24b according to FIG. 4. An opening 37 is arranged within the Venturi nozzle 36 in the exemplary embodiment according to FIG. 4 such that the discharge line 24b comprises an opening 37 in the region of the Venturi nozzle 36. In this context, the opening 37 is part of the Venturi nozzle 36 and is a particular design of the Venturi nozzle 36.

The design of the other components of the sample holder 21b shown in FIG. 4, for example the accommodation device 23, the hybrid unit 34, and the contact block 22, correspond to the design of the components described above with reference to the sample holder 21a according to FIG. 3. Please refer to the explanations provided with reference to FIG. 3 and apply these accordingly to the explanations provided with reference to FIG. 4.

FIG. 5 shows another alternative embodiment of a sample holder 21c, wherein identical components are provided with the same reference numbers and new components are provided with new reference numbers.

The sample holder 21c shown in FIG. 5 is described in the following in appropriate manner, such that changes as compared to the sample holder 21a described in FIG. 3 are described first. The sample holder 21c shown in FIG. 5 comprises no gas filter 32b and no gas filter 32a in the form of an intermediate filter. Moreover, the sample holder 21c comprises no gas exit opening 33. Moreover, the sample holder 21c shown in FIG. 5 comprises no connections in the form of a switching cable connection 27b, a gas connection 25b, and a signal cable connection 29b. Namely, the sample holder 21c shown in FIG. 5 only comprises a signal cable 29a exiting from the sample holder 21c, a switching cable 27a, and a gas feed line 25a, which each are guided out of the sample holder 21c in the region of the accommodation device 23. These extend, for example, directly into the adjacent lance. However, it is feasible that these can be connected outside of the sample holder 21c, for example inside the lance, to other cables or lines by a plug connector or the like (not shown here).

Moreover, a vacuum chamber 38 is arranged inside the sample holder 21c. The volume of the vacuum chamber 38 in the present exemplary embodiment is approx. 0.3 l. The vacuum chamber 38 is formed in the sample holder 21c in that a part, which is arranged in the sample holder 21c, of the discharge line 24b that is connected to the switch 26 has a larger diameter than the other parts of the discharge line 24b. Accordingly, the vacuum chamber 38 is formed at the location of the larger diameter. In this context, the vacuum chamber 38 is connected to a gas suction line 39 as a further line that is present, wherein the gas suction line 39 is connected to a vacuum pump (not shown here).

The other components of the sample holder 21a described in FIG. 3 are also present in the sample holder 21c and are not described again according to explanations provided above. These can be applied accordingly.

The sample holders 21a, 21b, 21c described in FIGS. 3 to 5 can be used, for example, in a device for implementing sampling processes in molten metals using a lance, in particular in molten steels using a sub-lance. A device of this type and a corresponding lance, in particular a sub-lance, are not shown in FIGS. 3 to 5. However, it is sufficiently well-known that a lance comprises a lance body that is arranged in a device of this type.

According to the invention, a sample holder 21a, 21b, 21c according to any of the explanations with regard to FIGS. 3 to 5 can be connected to one end of the lance body and a sampler 1 according to FIG. 1, in particular for use in molten steel, can be connected to it. In the present exemplary embodiment, the device comprises, by the corresponding sample holder 21a, 21b, 21c according to FIGS. 3 to 5, a feed line 24a for supplying gas via the contact block 22 into the sampler 1, and a discharge line 24b for drawing off gas via the contact block 22 from the sampler 1, and a gas line 24c that is connected to the sample chamber 2.

The sample holder 21a, 21b, 21c used in the device not shown in FIGS. 1 to 5, has a length L measured in axial direction from the contact block 22 to the opposite side of the sample holder 21a, 21b, 21c. The switch 26 in the corresponding sample holder 21a, 21b, 21c is therefore arranged at a distance of 0.1× its length L from the end of the contact block 22 in the present exemplary embodiment.

According to the explanations provided above referring to FIGS. 3 to 5, the sampler 1 and the sample holder 21a, 21b, 21c can be connected by a carrier tube 19 made of cardboard, wherein the carrier tube 19, which touches against the sampler 1 in the region of the seal 30 on the contact block 22, is not shown in FIGS. 3 to 5 according to explanations provided above.

The method for removing a sample 3, formed from a molten steel 4, from a sampler 1 according to FIG. 1 is described as in the following as a particularly preferred embodiment using a sample holder 21a according to FIG. 3 and a sampler 1 according to FIG. 1.

For this purpose, a sub-lance (not shown in FIG. 3) is connected to the sample holder 21a, wherein the connection is situated in the region of the accommodation device 23. The corresponding signal cable connection 29b, the switching cable connection 27b, and the gas connection 25b are each connected to corresponding connectors within the sub-lance. The sampler 1 according to FIG. 1 is positioned in the region of the contact block 22 of the sample holder 21a, wherein the gas socket 31 is arranged in the connector 9 of the sampler 1 in appropriate manner, such that a gas-tight connection between sample holder 21a and sampler 1 is generated. A carrier tube 19 made of cardboard is positioned between sampler 1 and accommodation device 23 of the sample holder 21a as part of the sample holder 21a, such that the sample holder 21a is situated between sampler 1 and the end of the carrier tube 19. The carrier tube 19 is firmly connected to the accommodation device 23, for example by an engagement connection of the type of a thread, wherein the accommodation device 23 then is pressed firmly into the carrier tube 19 by a corrugated surface.

The sampler 1 situated inside the device is then immersed into a molten steel indicated in FIG. 1, wherein the inert gas is supplied, before immersion, by the feed line 24a, which is supplied with a flowing inert gas by the gas feed line 25a, which was supplied earlier by the sub-lance. The inert gas supplied by the feed line 24a is then conducted through the switch 26, which is in position A, and thus into the gas line 24c, wherein the hybrid unit 34 also is situated in the region of the gas line 24c according to explanations provided above. When the inert gas flows through the gas socket 31 into the sampler according to the explanations provided referring to FIG. 1, the gas ultimately only enters into the filling tube 5 at first. After immersion of at least the sampler 1 into the molten steel 4 and melting of the protective cap 14 and cover 13 according to the explanations provided referring to FIG. 1, gas exits from the filling tube 5 when the sampler 1 is situated in the molten steel 4. Concurrently, the signal cable 29, which also is routed through the hybrid unit 34 into the thermocouple 12 of the sampler 1, is used to measure and analyze the temperature of the molten steel and the position of the sampler 1 in the molten steel, wherein the analysis is done using an external unit (not shown here) that analyzes the data transferred by the sample holder 21a and sub-lance (not shown here) by the signal cable 29.

After the sampler 1 reaches the appropriate position in the molten steel 4, the supply of gas through the feed line 24a is interrupted according to explanations provided above by switching switch 26 into position B. This interrupts the supply of gas through the feed line 24a. In the present exemplary embodiment, the switch 26 in the sample holder 21a is switched appropriately, such that the sample chamber 2 of the sampler then fills with molten steel 4. Then the sampler 1 and the carrier tube 19 and the sample holder 21a are removed again from the molten steel using the mobile sub-lance in the device after the sample chamber 2 has completely filled-up with molten material. For cooling of the sampler 1 and sample chamber 2, the switch 26 is then switched or switched back from position B to position C, which corresponds to position A in the exemplary embodiment according to FIG. 3. This allows the sample chamber 2 to be cooled by the supplied gas. The cooling process is described in detail in the exemplary embodiment of FIG. 1. The switch 26 is switched by the switching cable 27a by which the switch 26 can be switched.

Switching the switch 26 from position A to position B, gas exits through the sampler 1 into the sample holder 21a, whereby the gas then flows through the gas line 24c and the hybrid unit 34, then through the gas filter 32b and is finally conducted through the switch 26. With the switch being in position B, the gas then flows out through the additional gas filter 32a in the form of an intermediate filter and through the discharge line 24b through the gas exit opening 39. Due to the exiting of the gas, the sample chamber 2 can fill-up with molten material. This is described in detail in the exemplary embodiment of FIG. 1. No vacuum or negative pressure according to the previous embodiments is generated in this context. Accordingly, at least the amount of gas that is present in the sample chamber 2 and the filling part 5 exits from the gas exit opening 39.

The switch 26 is switched from position A to position B when a temperature of, for example 1100° C. is measured by the thermocouple 12. Alternatively or in addition, the lance position can be measured by electrical means or by the pressure in the molten steel using the position of the sampler 1.

The process of sampling from a molten steel 4 described above can also be implemented by a sample holder 21b according to FIG. 4.

According to the embodiment of FIG. 3 according to explanations provided above, the sample holder 21a is replaced by the sample holder 21b in a further embodiment. In the following, the flow of the gas through the sample holder 21b is described with a focus on the differences as compared to the previous embodiment with sample holder 21a.

Once the connectors according to FIG. 4 fitting the sub-lance or the sampler according to FIG. 1 have been connected, the inert gas flows through the gas feed line 24d into the feed line 24a and the discharge line 24b. The gas flowing through gas feed line 25a then flows, on the one hand, through the feed valve 35 into the switch 26 which is in position A. The gas flowing in can therefore flow through the switch 26 and the gas filter 32b through the hybrid unit 34 into the sampler 1. On the other hand, gas supplied from gas feed line 25a flows through the discharge line 24b through the Venturi nozzle 36 concurrently, such that a negative pressure is generated between Venturi nozzle 36 and switch 26 due to the special embodiment of the Venturi nozzle 36. The gas supplied by the discharge line 24b is made to exit out of opening 37 in this context.

In order to fill the sample chamber 2, the switch 26 is switched from position A to position B, such that the gas flowing through the feed line 24a can no longer flow into the gas feed line 24c due to the switch being in position B. Only the gas flowing through the gas feed line 25a can exit through the discharge line 24b and the Venturi nozzle 36 through the opening 37, wherein a negative pressure continues to be generated between Venturi nozzle 36 and switch 26 and is transferred to gas line 24c. As a result, a negative pressure is generated in the sample chamber 2 and is used to aspirate molten material into the sample chamber 2 by the Venturi nozzle 36. After the sample chamber 2 is filled with molten material, the switch 26 is switched back into position A, such that the sample chamber 2 can be cooled by the gas supplied through feed line 24a.

The removal of the sample chamber and/or sampler 1 from the molten material has been described in detail above.

The sampling from a molten steel 4 by a sample holder 21a described above can also be implemented by a sample holder 21c according to FIG. 5. In the following, just the sample holder 21c in a special embodiment situated between sampler 1 and sub-lance in the device is described in detail with changes or other technical implementations being emphasized in detail.

According to FIG. 5, an inert gas flows through the feed line out of the sub-lance through the switch 26 and into the gas line 24c into the sampler 1 according to FIG. 1. In order to fill the sample chamber 2, the switch 26 is switched from position A to position B, such that the inert gas, which previously was guided through the feed line 24 exclusively, is blocked due to the switch 26 having been switched to position B. Accordingly, gas can flow through the gas line 24c through the switch 26 into the vacuum chamber 38, in which a negative pressure has been generated. The negative pressure in the vacuum chamber 38 was generated earlier, for example, via the gas suction line 39 and by a vacuum pump. Accordingly, the molten material 4 is aspirated into the sample chamber 2 by the negative pressure from the vacuum chamber 38 once the switch 26 is switched from position A to position B. For cooling, the switch 26 is switched back into position A such that inert gas can flow again through the feed line 24a and then through the gas line 24c into the sampler 1, such that the sample chamber 2 is cooled.

The immersion of the corresponding devices, in particular with reference to the sample holder 21b and 21c, has been described in detail for sample holder 21a and is applicable accordingly to the sample holders according to 21b, 21c. Moreover, the process of pulling the sampler 1 according to FIG. 1 out of the molten material 4 has been described in detail, such that this can also be applied to the sample holders 21b and 21c.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sampler (1, 1a) comprising:
   a sample chamber (2) for a sample (3) forming from a molten material;
   at least one lower cooling body (6);
   at least one upper cooling body (8);
   at least one inner cooling body (7); and
   at least one filling part,
      wherein the sample chamber (2) is surrounded jointly at least by the at least one lower cooling body (6) and the at least one inner cooling body (7), such that at least the sample chamber (2) can be cooled by at least the at least one lower cooling body and the at least one inner cooling body,
      wherein the at least one filling part is connected to the sample chamber (2) and merges into the sample chamber (2) by a filling opening (5a),
      wherein each of the at least one lower cooling body, the at least one upper cooling body and the at least one inner cooling body comprises an outer surface (7a, 8a), and
      wherein the sampler (1, 1a) comprises, between a region of the outer surface (7a) of the at least one inner cooling body (7) and a region of the outer surface (8a) of the at least one upper cooling body (8) opposite to the outer surface (7a) of the at least one inner cooling body (7), at least one gap (11) for conducting at least one gas, a volume of the respective cooling bodies (6, 7, 8) being larger than a volume of the at least one gap (11).

2. The sampler (1, 1a) according to claim 1, wherein at least the at least one lower cooling body (6) and the at least one inner cooling body (7) form a wall of the sample chamber (2), wherein the wall is formed by a region of the respective outer surface of the at least one lower cooling body (6) and of the at least one inner cooling body (7), such that the sample chamber (2) comprises a hollow space formed between the at least one lower cooling body (6) and the at least one inner cooling body (7).

3. The sampler (1, 1a) according to claim 1, wherein at least one of the at least one lower cooling body, the at least one upper cooling body and the at least one inner cooling body comprises at least one ventilation opening (16).

4. The sampler (1, 1a) according to claim 3, wherein the at least one ventilation opening (16) is closed by at least one closure, optionally a membrane (17), which can be opened while or after the sample chamber (2) is being filled with the molten material.

5. The sampler (1, 1a) according to claim 4, wherein the at least one closure comprises at least one plastic connection.

6. The sampler (1, 1a) according to claim 4, wherein the at least one closure has a pressure resistance of approximately 0.5 bar to approximately 4 bar.

7. The sampler (1, 1a) according to claim 4, wherein the at least one closure has a temperature resistance of approximately 50° C. to approximately 90° C.

8. The sampler (1, 1a) according to claim 3, wherein a diameter of the at least one ventilation opening (16) is approximately 0.7 mm to approximately 1.3 mm.

9. A method for sampling from molten material having a melting temperature of more than 600° C., the method comprising positioning the sampler according to claim 1 at one end of at least one of a lance and a carrier part and immersing the sampler into the molten material, subsequently filling the sample chamber of the sampler with molten material, and then pulling at least the sample out of the molten material by the sampler, wherein the at least one gas is supplied into the sampler before immersing the sampler, wherein the at least one gas flows out again from the sampler through the at least one filling part, the sampler is subsequently immersed into the molten material, the supply of gas is then changed, followed by the sample chamber filling up with molten material, and gas is then supplied again into the sampler during or after the sample chamber fills with molten material, such that at least the sample chamber is cooled by the supplied gas.

10. The method according to claim 9, wherein the at least one gas flows through the at least one gap between at least the at least one inner cooling body and the at least one upper cooling body.

11. The method according to claim 9, wherein the sample is held by the at least one lower cooling body.

12. The method according to claim 9, wherein the sample is supplied to an analytical facility while it is in the sampler.

13. The method according to claim 9, wherein the at least one inner cooling body is held by the at least one upper cooling body.

14. The method according to claim 9, wherein the at least one gas flows out only through the at least one filling part before the molten material fills into the sample chamber, and the at least one gas flows out through at least one ventilation opening while or after the molten material fills into the sample chamber.

15. The method according to claim 14, wherein the at least one gas flowing out through the at least one ventilation opening is discharged through at least one gas exit opening for discharging the supplied gas from the sampler.

16. The method according to claim 14, wherein the at least one ventilation opening is closed by at least one closure, and wherein the at least one closure becomes permeable to gas while or after the molten material is filled into the sample chamber, by at least one of the temperature of the molten material and the pressure of the supplied gas.

17. The method according to claim 14, wherein, after filling the sample chamber with molten material, the newly supplied gas flows through the at least one gap and then flows through the at least one ventilation opening out of the sampler, wherein this cools down the temperature of the sample.

* * * * *